(12) United States Patent
Wallace

(10) Patent No.: US 6,468,284 B1
(45) Date of Patent: Oct. 22, 2002

(54) METHOD AND APPARATUS FOR VACCUM ASSISTED FETAL EXTRACTION

(75) Inventor: William Dean Wallace, Salt Lake City, UT (US)

(73) Assignee: Clinical Innovation Associates, Inc., Murray, UT (US)

(*) Notice: Subject to any disclaimer, the term of this patent is extended or adjusted under 35 U.S.C. 154(b) by 0 days.

(21) Appl. No.: 09/849,587

(22) Filed: May 4, 2001

(51) Int. Cl.$^7$ ................................................ A61B 17/42
(52) U.S. Cl. .......................................... 606/123; 606/122
(58) Field of Search .............................. 606/121–124, 606/119, 127, 34, 41, 32, 35, 42

(56) References Cited

U.S. PATENT DOCUMENTS

| | | | |
|---|---|---|---|
| 5,480,399 A | * | 1/1996 | Hebborn ...................... 128/908 |
| 5,569,265 A | * | 10/1996 | Elliott .......................... 606/122 |
| 5,649,934 A | * | 7/1997 | Smeltzer et al. ............. 606/122 |
| 6,074,399 A | * | 6/2000 | Wallace et al. .............. 606/122 |
| 6,355,047 B1 | * | 3/2002 | Wallace et al. .............. 606/122 |
| 6,361,542 B1 | * | 3/2002 | Dimitriu et al. ............. 606/119 |
| 6,402,741 B1 | * | 6/2002 | Keppel et al. ............... 128/903 |

OTHER PUBLICATIONS

Moolgaoker, Arvind S., et al., "A Comparison of Different Methods of Instrumental Delivery Based on Electronic Measurements of Compression and Traction," *Obstetrics & Gynecology*, vol. 54, No. 3, Sep. 1979, pp. 299–304.

* cited by examiner

*Primary Examiner*—Pedro Philogene
(74) *Attorney, Agent, or Firm*—TraskBritt

(57) ABSTRACT

A vacuum assisted fetal extraction apparatus and a monitoring device for use in conjunction therewith. The monitoring device includes a circuit including a timer operably coupled with a switch, which may comprise a differential pressure sensor. The switch is configured to be actuated by the formation of a vacuum to secure the fetal extractor to a fetus. At least partial release of the vacuum releases the switch to stop or pause the timer. The timer may be configured to be reset such that it only records or displays the duration of a specific application of the vacuum device, or it may be configured to record or display a cumulative duration based upon multiple applications of the vacuum device in an absolute sense or during a defined time period. Magnitude as well as the cumulative number of applications of an applied vacuum may also be measured and, optionally, displayed, as may the number of times traction force is applied to an infant during delivery.

80 Claims, 6 Drawing Sheets

METHOD AND APPARATUS FOR VACCUM ASSISTED FETAL EXTRACTION

BACKGROUND OF THE INVENTION

1. Field of the Invention

The present invention relates generally to methods and apparatus for extracting fetuses from the mother to facilitate delivery. The present invention relates more specifically to apparatus and methods for vacuum assisted fetal extraction and the monitoring of an applied vacuum used in such a procedure.

2. State of the Art

During childbirth, the birth mother often requires assistance in the delivery of the fetus. In certain, more extreme instances, such assistance may include surgical intervention known as a Caesarean section delivery. A Caesarean delivery involves making an incision in the abdomen and uterus and extracting the fetus through the incisions. In less extreme cases, assistance is provided through the use of various extraction tools or instruments. Typically, such instruments include either forceps or a vacuum cup device, either of which is used to grip the fetus' head to maneuver the fetus through the birth canal.

The use of forceps entails grasping and compressing the fetus' head between a pair of opposable members at the distal end of a scissors-like instrument and then maneuvering the fetus' head with the forceps. While the use of forceps allows for considerable manipulation of the fetus, the rigid instrument and force applied to the head by the physician's gripping of the proximal ends of the forceps to maintain secure contact with the fetus' head are potentially damaging to the soft and pliable head. Harm may also inadvertently come to the mother's body during manipulation of the fetus due to the unyielding nature of the forceps.

Vacuum assisted extraction devices comprise well known alternatives to forceps. Vacuum assisted fetal extractors, sometimes referred to in their simplest manifestation as obstetric vacuum cups, may be utilized in order to apply an externally created vacuum force to the head of the fetus to secure the extractor to the head for use as a traction device. Vacuum cups generally operate by placing the cup on the head of the fetus, mechanically evacuating air from the cup and simultaneously drawing the cup against a portion of the fetus' head. By so attaching the cup to the fetus' head, a traction force may be applied to the fetus such that it may be manipulated and the fetus pulled from within the mother's uterus in conjunction with the mother's contractions.

While vacuum assisted fetal extractors have provided many advantages in the delivery of a fetus from its mother, such devices also pose potential hazards if not properly utilized or adequately monitored during their use. Such hazards stem from the fact that the fetus' skull is soft and structurally weak and thus renders the head of the fetus susceptible to deformation or injury during childbirth.

Misapplication or improper use of a vacuum assisted fetal extractor may result in any of a number of injuries to the fetus. Such injuries might include, by way of example only, subdural hematoma, subgaleal hemorrhage, chignon, abrasions, as well as other, less common injuries. While not an exhaustive list, injuries of the foregoing type listed above may be the result of improper placement of the vacuum cup on the fetus' head, application of an excessive vacuum magnitude, or maintaining a vacuum for an excessive continuous duration. Injury may also occur as a result of maintaining a vacuum for an excessive cumulative duration either during a specified period of time (e.g., longer than 20–30 minutes) or as a total cumulative duration.

Additionally, the occurrence of one of the above-listed potentially injurious events may influence or magnify the effects of another. For example, the application of a vacuum of a greater magnitude may affect the maximum desirable duration of the applied vacuum, either for application over a fixed, specific period or for a cumulative duration.

Thus, it would be desirable to provide, in the art of vacuum assisted fetal extraction, a technique for monitoring the application of a vacuum force to a fetus' head to avoid or ameliorate potentially undesirable effects of the vacuum on the fetus. Such monitoring technique would preferably be effectuated through use of a device which is simple and reliable in design and in operation, adaptable to existing vacuum-type extraction devices, conducive to long-term storage and inexpensive to fabricate so as to enable its disposal after a single use.

Additionally, it would be advantageous to include with such monitoring technique the use of a representative, preferably automated index or scale resulting from a combination of multiple, potentially harmful factors or parameters attendant to vacuum assisted delivery such that monitoring of such multiple factors or parameters during a procedure is simplified.

BRIEF SUMMARY OF THE INVENTION

In accordance with one aspect of the invention, a monitoring device is provided for use with vacuum assisted fetal extractors. The monitoring device includes a circuit configured to provide, at least in part, a timing function or timer. An output unit such as, for example, a liquid crystal display (LCD) is operably coupled to the circuit to receive a signal from the circuit which is indicative of one or more durations as measured by the timer. A switch is also operably coupled to the circuit and to a vacuum reservoir such that creation of a vacuum in the vacuum reservoir by a vacuum source to be communicated to a cup or other structure used to form a vacuum chamber with the fetus' head to grip the head actuates the switch and activates the timer. Full or partial (as by relaxation of the vacuum below a selected threshold) release of the vacuum in the vacuum reservoir likewise releases the switch such that the timer is deactivated. The output unit may display or record duration of an applied vacuum, or both display and record same. The monitoring device and output unit may include additional features such as a pressure (vacuum) sensor operably coupled to the circuit and output unit to enable displaying and/or recording the magnitude of vacuum being applied in either continuously or in terms of peak figures. The pressure sensor may be used in lieu of the switch to activate and deactivate the timer at the same or different levels of pressure or vacuum. The monitoring device may be configured to time the duration of a specific application of vacuum or to time on a cumulative basis to sum the durations of multiple applications of the vacuum. Furthermore, if the monitoring device is configured to time duration of vacuum application on a cumulative basis, the cumulation may represent an absolute cumulative total for all applications of the vacuum, or it may represent a cumulative duration of vacuum applications within a specified rolling time period such as, for example, the immediately preceding hour. The monitoring device may also be configured to record and keep track of the number of times a vacuum is generated and released, as well as the number of times traction is applied to the infant. Application of traction may be indicated through, for example, detection of fluctuations in vacuum level as the infant is pulled, by the number of vacuum increase/decrease cycles detected, or through use of a force sensor. The circuit may further include one or more alarms responsive to the timing function or the pressure sensor to alert the clinician as to when a vacuum duration or magnitude has been, or is about to be, exceeded.

In accordance with another aspect of the present invention, a second embodiment of a monitoring device is provided for use with vacuum assisted fetal extractors. The second embodiment may be configured as described above with respect to the first embodiment. However, in the second embodiment, the output unit, such as, for example, an LCD, may be operably coupled to the circuit to receive a signal from a processor associated with the circuit which is indicative of a transfer function representative of an index or scale indicative of the combined effects on the fetus' head of, for example, at least a magnitude or magnitudes of the applied vacuum as measured by the pressure sensor and the duration or some cumulative durations of the applied vacuum as measured by the timer. The output unit may also display or record the durations, as well as magnitudes, of the applied vacuum.

In accordance with another aspect of the present invention, a vacuum assisted fetal extraction apparatus is provided. The vacuum assisted fetal extraction apparatus includes a vacuum cup or other structure configured to be applied to the head of a fetus to form a chamber therewith and a vacuum source operably coupled to the vacuum cup to selectively create a vacuum when the cup is placed against the fetus' head. The vacuum assisted fetal extraction apparatus also includes a monitoring device similar to one of those described above.

In accordance with yet another aspect of the invention, a method is provided for using a vacuum assisted fetal extraction apparatus. The method may include applying a vacuum one or more times to secure the apparatus to a portion of the fetus, measuring the magnitudes of A the vacuum as applied and communicating the measurements to the clinician. The duration or durations of the applied vacuum may also be measured and then communicated to the clinician. The method may also include measuring both magnitude and duration of vacuum application, as well as clocking total duration and number of multiple vacuum applications either absolutely or within a defined time frame. The method may further include alerting an operator with an audible or visible alarm when a measured value has been or is in danger of being exceeded. Furthermore, the method may include using a combination of vacuum magnitude and duration measurements in a composite index or scale to indicate, through an output responsive to the value of the composite index or scale responsive to application of a vacuum to the fetus' head, either safe use of the vacuum assisted delivery device or a potential for an injury-causing event if the vacuum is not released or relaxed.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
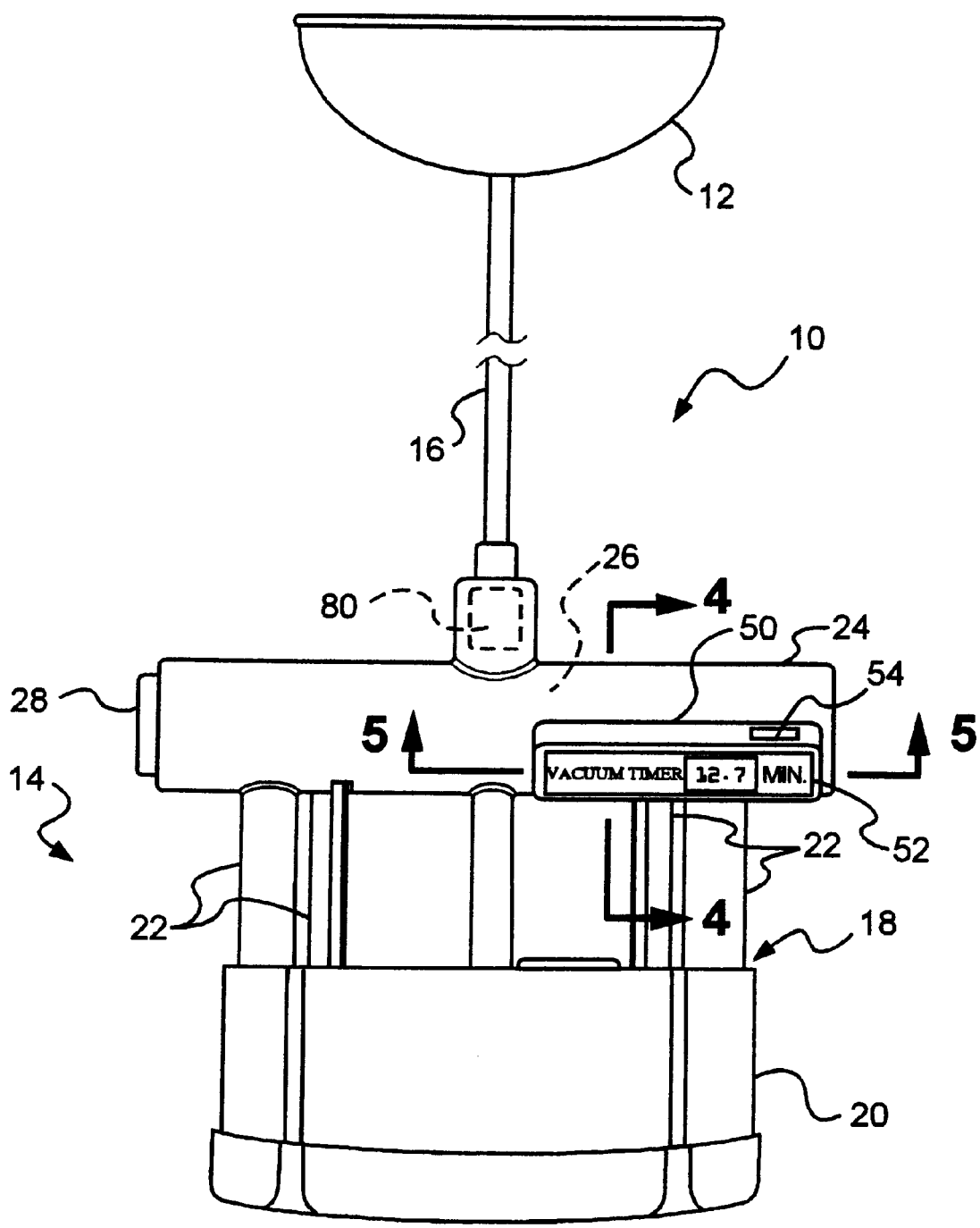
FIG. 1 is a vacuum assisted vaginal extraction apparatus according to one embodiment of the present invention.

Turning to the drawings, wherein like parts in the various figures are indicated with like numerals and referring first to FIG. 1, an exemplary embodiment of a vacuum assisted fetal extraction apparatus 10 is shown. The extraction apparatus 10 includes a vacuum cup 12, which is configured with an interior cavity to be applied to a portion of the fetus, namely the fetus' head, forming a chamber therewith by which a vacuum is applied to the fetus' head. The vacuum cup 12 is sealingly connected to a hand pump 14 by a section of tubing 16. Such tubing 16 may be of a robust material and formed as a structural member to assist in manipulation of the fetus once a vacuum has been applied through the cup 12.

The hand pump 14 may be structured such as is disclosed in U.S. Pat. No. 6,074,399 to Wallace et al., assigned to the assignee of the present invention and the disclosure of which is incorporated by reference herein. Generally, the hand pump 14 includes a reciprocable pumping assembly 18 including a palm chamber 20 which is slidably disposed on guide members 22. The palm chamber 20 houses various seals and valves (not shown) arranged in check valve fashion and configured to draw air in a single direction when the reciprocable pump assembly is actuated by gripping and releasing with the user's hand as is understood by those of ordinary skill in the art. Housed in a handle or grip 24 is a vacuum reservoir 26 as depicted in cross section in FIG. 4. A vacuum release element 28 is positioned on one end of the handle 24 to allow an operator to open a valve by depressing vacuum release element 28 against a resilient loading to a closed position and thus release or relax a vacuum applied by vacuum cup 12 to the head of the fetus at any time during utilization of the apparatus 10. While the vacuum release element 28 is shown to extend or protrude from one end of the handle 24 for clarity of illustration, it may be preferred to have the release element 28 recessed to avoid accidental and premature release of a vacuum from vacuum cup 12.

Figure 2:
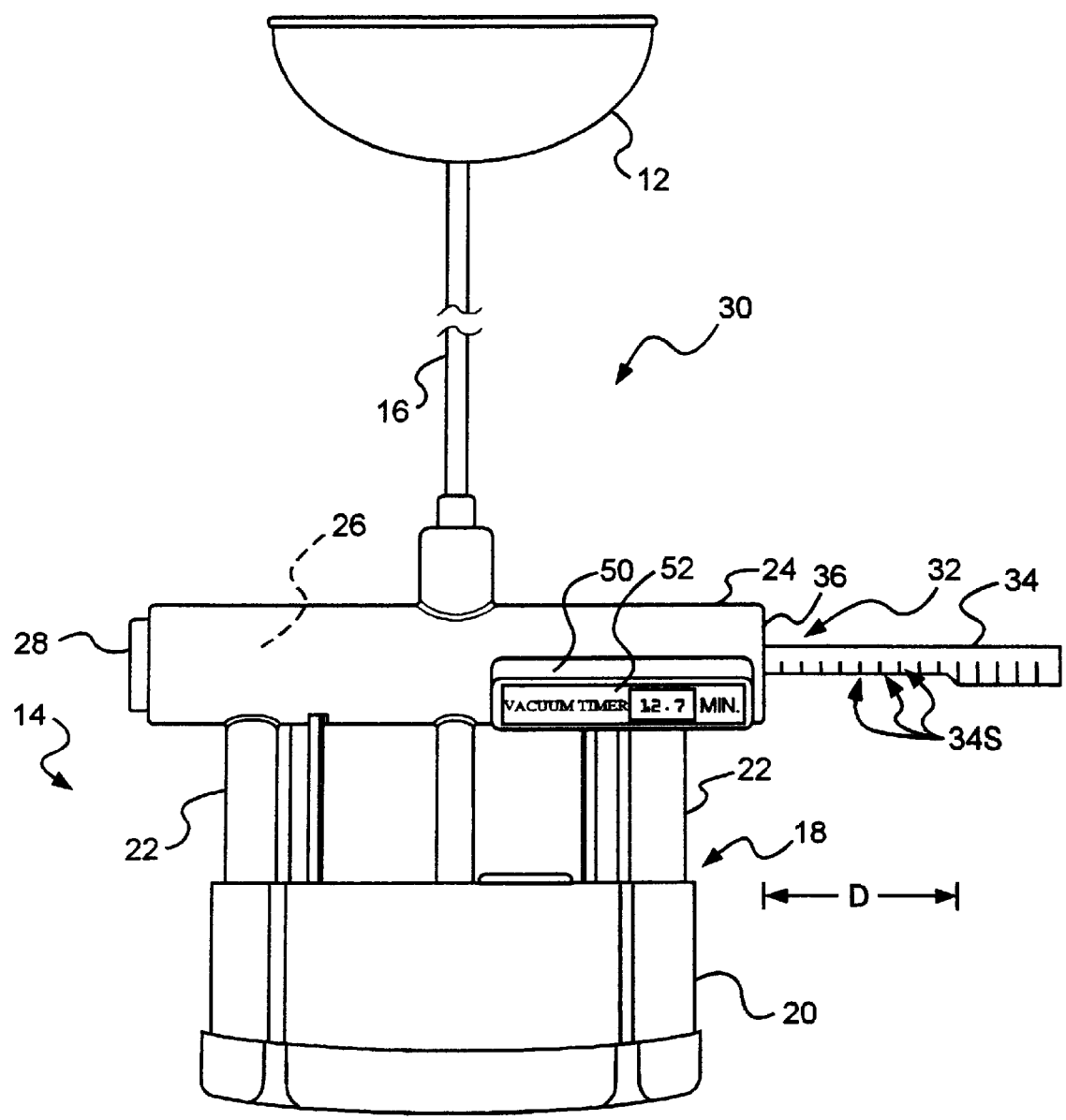
FIG. 2 is a vacuum assisted vaginal extraction apparatus according to an alternative embodiment of the present invention.

FIG. 2 depicts a vacuum assisted fetal extraction apparatus 30 similar in structure to that of FIG. 1 and which includes all the aforementioned features as well as a mechanical, spring-biased vacuum indicator 32. Indicator 32 employs a spring force which may be substantially linearly overcome by vacuum applied to a cylinder bore comprising the interior wall of vacuum reservoir 26 within which a spring (typically coil) biases a piston slidingly sealed against the cylinder bore wall. The indicator 32 includes a rod 34 secured to the piston and extendable outwardly from vacuum reservoir 26 parallel to the axis of handle 24 and at one end thereof. Rod 34 includes a visual scale 34s marked thereon representative of a calibrated level of vacuum as applied by the vacuum assisted extraction apparatus 30. As a vacuum is applied by the apparatus 30, the rod 34 is drawn inwardly into the vacuum reservoir 26 and the magnitude of vacuum is indicated, such as in mm Hg, by discerning the position of the indicia of scale 34s with respect to an outer edge 36 of the handle 24. At a location along its length corresponding to a predetermined vacuum, the diameter or width of rod 34 may increase, as shown in FIG. 2, to indicate a certain magnitude of vacuum and trip a simple mechanical switch to actuate a timer, as discussed in more detail below. With such an arrangement, the need for a vacuum-responsive switch or sensor is eliminated. In all other regards, the apparatus 30 shown in FIG. 2 may be constructed similar to the extraction device 10 disclosed in FIG. 1. It is noted that the apparatus 10 of FIG. 1 may also have the capability of indicating the level of an applied vacuum, which feature shall be discussed in more detail below.

Figure 3:
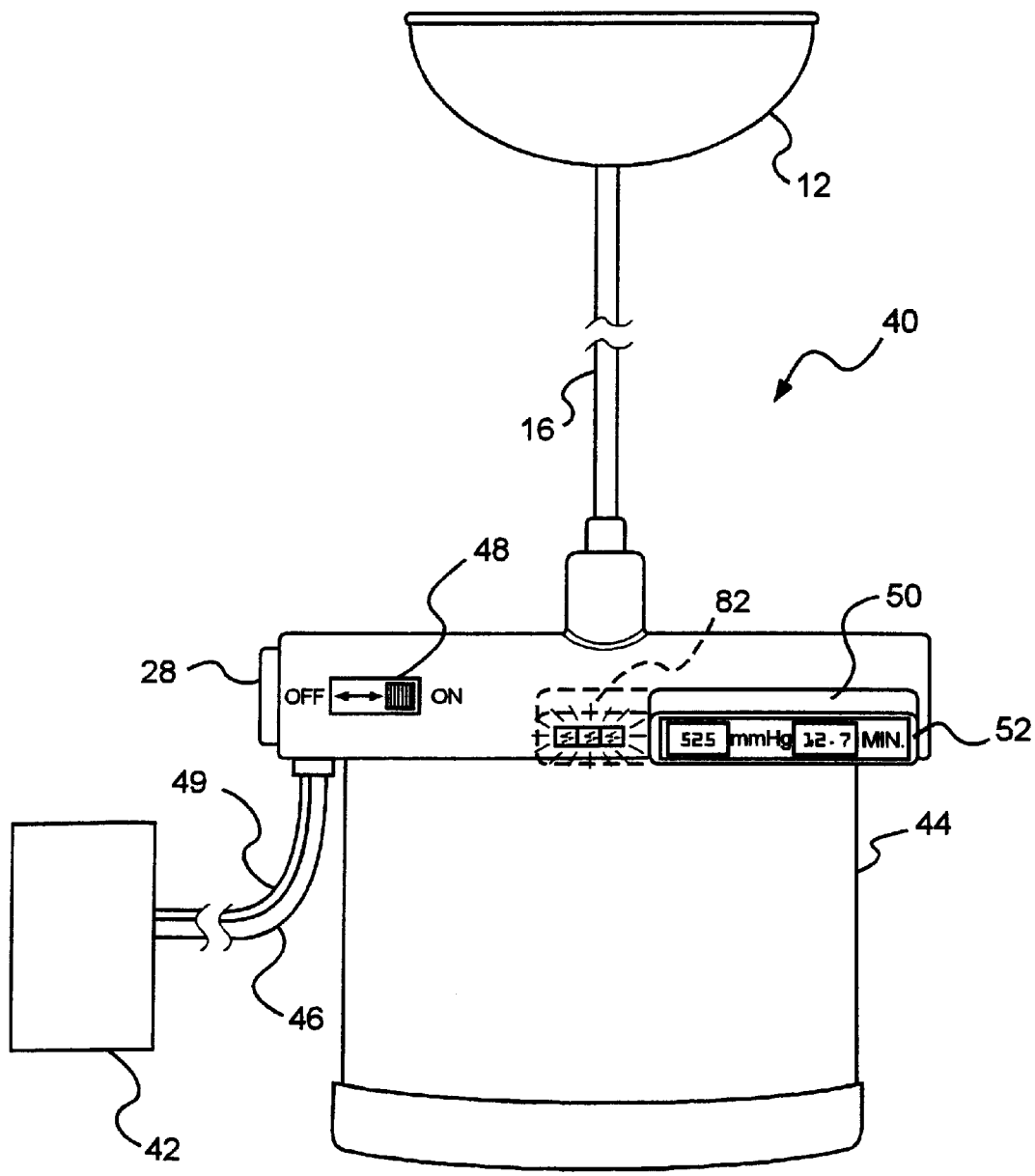
FIG. 3 is a vacuum assisted vaginal extraction apparatus according to yet another alternative embodiment of the present invention.

FIG. 3 illustrates yet another vacuum assisted fetal extraction apparatus 40 which employs a different vacuum source 42 than do the embodiments of FIGS. 1 and 2. The apparatus 40 of the present embodiment includes a vacuum cup 12 sealingly connected to a gripping member 44 through a section of tubing 16. However, in this instance, the gripping device does not include a hand pump. Rather, an independent vacuum source 42, such as an electric pump, is connected to the vacuum reservoir 26 by a second section of tubing 46. While depicted to be external to the vacuum reservoir 26, the vacuum source 42 could be integrated with the vacuum reservoir 26 or the gripping member 44. However, such an alternative increases the cost of the apparatus and may render it unsuitable for single use followed by disposal. The vacuum source 42 may be actuated by a control button 48 associated with a simple on/off electrical switch and located on the gripping member 44, the switch being connected to vacuum source 42 by cable 49 running adjacent second section of tubing 46.

Each of the three disclosed embodiments of a vacuum assisted fetal extraction apparatus according to the invention additionally include a monitoring device 50 according to the invention. Because operation of the monitoring device 50 is similar among the disclosed extraction apparatus embodiments, it will be discussed primarily with reference to FIG. 1 along with FIGS. 4 and 5 as indicated by representative section lines shown in FIG. 1. In the apparatus of FIG. 1, the monitoring device 50 is shown to be located on the handle 24 adjacent and exterior to the vacuum reservoir 26. As used herein, the term "vacuum reservoir" is not limited to a particular or dedicated chamber, but encompasses any portion of a vacuum assisted fetal extraction apparatus of any configuration wherein a vacuum is present or created and may be used in securing the apparatus to a fetus. The monitoring device 50 includes an output unit preferably in the form of a visual display 52. The visual display 52 may include, by way of example only, a liquid crystal display (LCD), one or more light emitting diodes (LED), or a mechanical, analog type display. The visual display 52 may also, as desired, combine display types for various purposes as will be discussed in more detail below. In addition to a visual display 52, or as a possible alternative, an output jack or port 54 may be incorporated into the monitoring device 50. An output port allows interconnectivity through, for example, an RS-232 interface with additional instruments or recording devices to receive signals from monitoring device 50 and may also be used to supply power in the form of line voltage (optionally through a transformer) to monitoring device 50 to eliminate the need for an internal battery.

Figure 4:
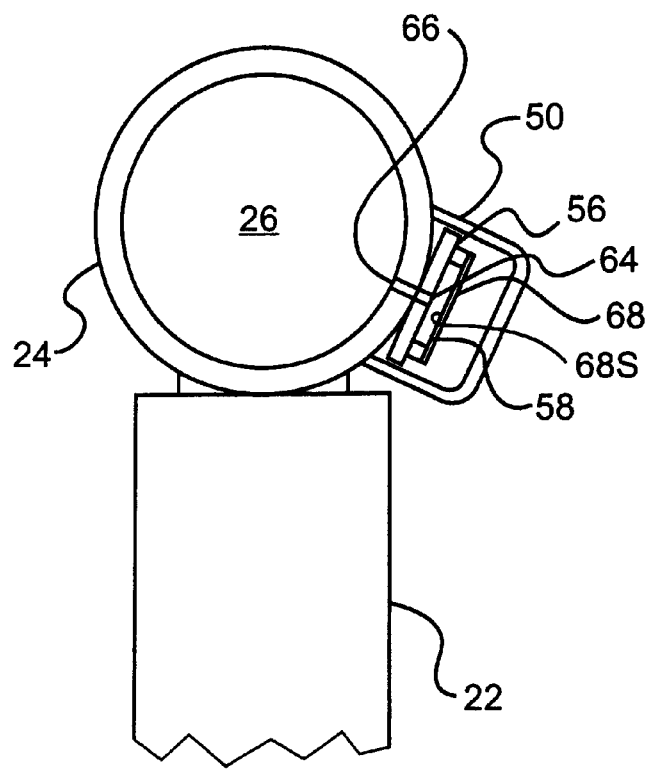
FIG. 4 is a partial sectional view of a monitoring device used in conjunction with a vacuum assisted vaginal delivery device as depicted by section 4—4 in FIG. 1.
Figure 5:
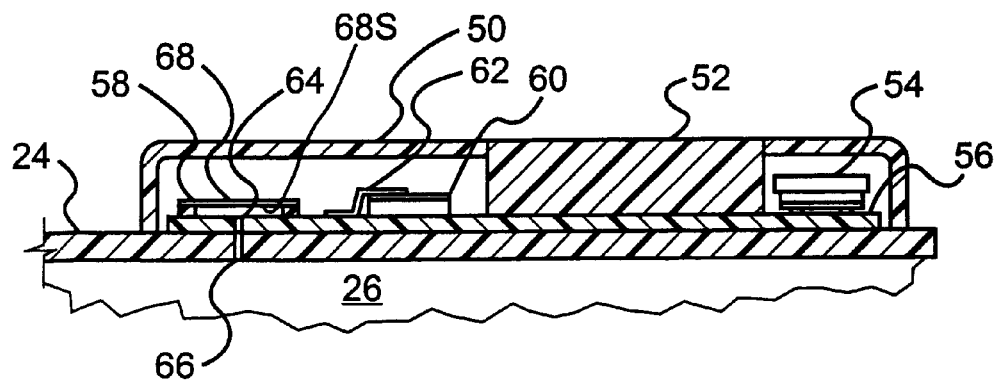
FIG. 5 is a partial sectional view of a monitoring device used in conjunction with a vacuum assisted vaginal delivery device as depicted by section 5—5 in FIG. 1.

Referring more specifically to FIGS. 4 and 5, the visual display 52 and/or output port 54 are operably connected to a circuit board 56. Also connected to the circuit board 56 is a switch, shown as a vacuum responsive switch 58, and an electrical source such as a watch-type "button" battery 60. A conductive element 62 helps to secure battery 60 in place and to electrically interconnect one pole of the battery 60 with the circuit board 56. The vacuum switch 58 resides above, and the periphery thereof is sealed over, a small aperture or port 64 formed through the circuit board 56. The aperture 64 is aligned with a cooperating aperture or port 66 formed through the wall of handle 24 of the apparatus 10 to create a sealed passage between vacuum switch 58 and vacuum reservoir 26 within handle 24. The vacuum switch 58 may be of the type including a diaphragm 68 having an electrically conductive interior surface 68s which, upon application of a vacuum, deflects downward to touch and bridge, or close, normally open contacts of the vacuum switch 58, completing a circuit. The vacuum switch 58 may be, and preferably is, calibrated so as to close upon experiencing a specified pressure differential between the exterior of diaphragm 68 exposed to ambient atmospheric air pressure and the interior thereof, which is in communication with vacuum reservoir 26. For example, the vacuum assisted fetal extraction apparatus may be utilized at an applied vacuum level, relative to ambient atmospheric, of approximately 450 mm Hg, with vacuum switch 58 calibrated to close at substantially 450 mm Hg pressure differential. However, it may be desirable to track the application of a vacuum at even lower levels, for example, 300 mm Hg, or even as low as 100 to 150 mm Hg.

It is noted that while the vacuum switch 58 is disclosed in terms of including a vacuum-responsive diaphragm closing, upon deflection, normally open contacts, such a switch is exemplary and should not be considered limiting of the present invention in any sense. Alternative switches are contemplated as having utility. For example, as noted above and with regard to the embodiment of FIG. 2, a mechanically actuated switch might be coupled with the spring-loaded vacuum indicator 32 such that the switch is actuated when rod 34 is drawn into vacuum reservoir 26 a sufficient distance D to close contacts on the interior wall thereof and to open contacts upon relaxation of the vacuum to a magnitude insufficient to overcome the spring force.

Figure 6:
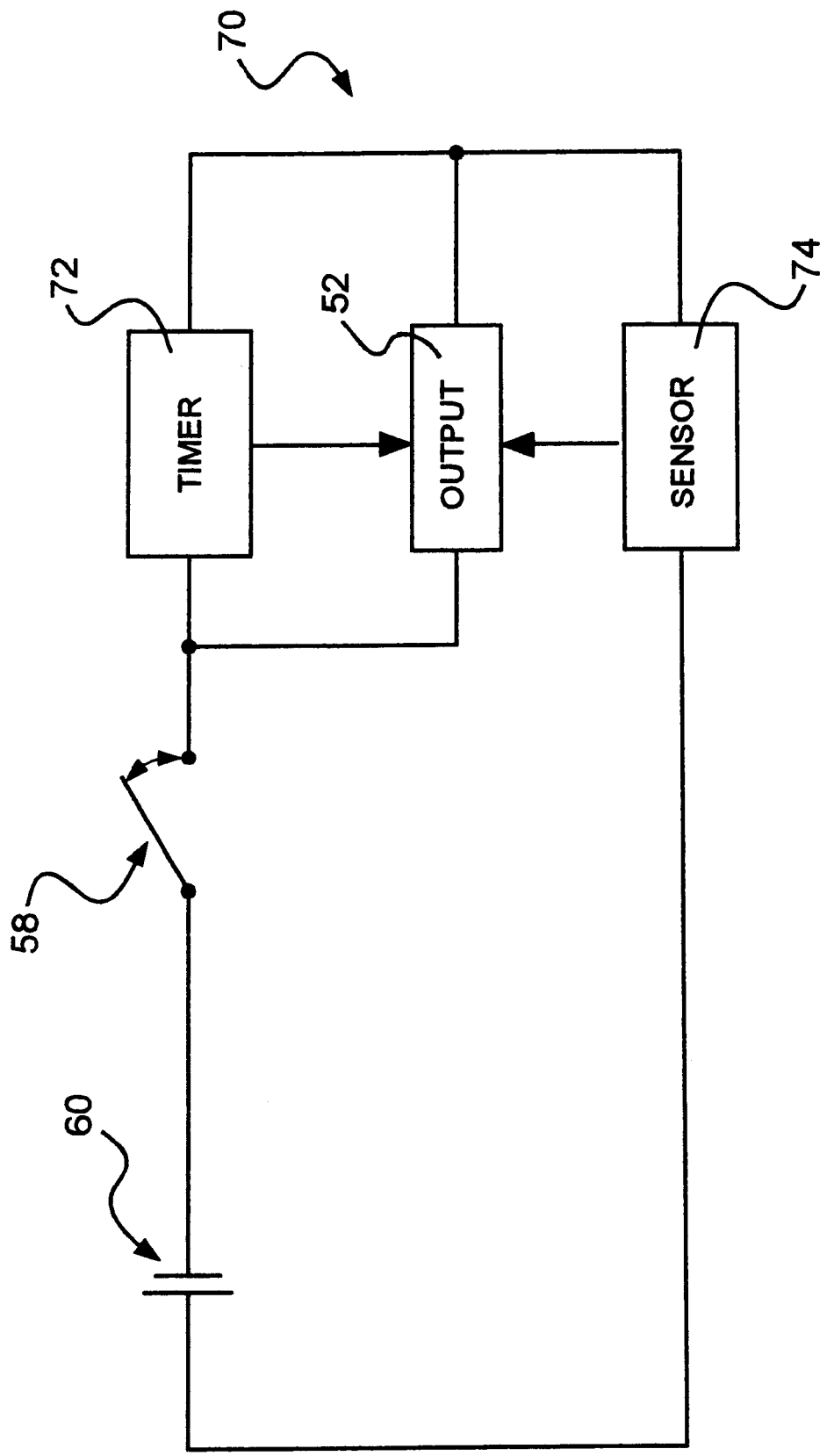
FIG. 6 is a simplified electrical circuit according to one embodiment of the present invention.

Upon the closing of the vacuum switch 58 or other alternative switch, a circuit powered by the battery 60 is completed. A simplified exemplary circuit 70 according the present invention is shown schematically in FIG. 6. The circuit 70 is at least partially configured to include a timer 72. Timer 72 may incorporate a microprocessor used to control display 52 and perform other functions. Upon activation of the circuit 70 responsive to closure, for example, of vacuum switch 58, the timer 72 begins to clock the duration of circuit operation. Optionally, and in lieu of vacuum switch 58 or another vacuum-responsive switch assembly, a pressure or vacuum sensor 74 may be employed with circuit 70 to activate and deactivate timer 72. The number of applications of vacuum to the infant thus may also be easily tracked by the number of times the timer 72 is activated and then deactivated. If desired, and as discussed further below, in more sophisticated embodiments of monitoring device 50, the output signal of pressure sensor 74 may be employed to activate timer 72 at one threshold magnitude of applied vacuum and to deactivate it at a different, lower magnitude. A microprocessor associated with the timer or otherwise located in the circuit may be employed to use the output of pressure sensor 74 to provide logic control and display. The sensor 74 may comprise an electronic sensor in the form of a pressure transducer as known in the art coupled to the vacuum reservoir 26 in the manner of vacuum switch 58 to directly measure the level of vacuum applied to the fetus' head through vacuum cup 12 and output a corresponding signal. Alternatively, in the case of the embodiment shown in FIG. 2, the vacuum sensor may comprise spring-biased vacuum indicator 32 and be configured to operate in the manner of a linear rheostat, the output of which would vary with the longitudinal position of rod 34 with respect to handle 24. Also included in the circuit 70 is an output unit such as the visual display 52. The output unit is configured to receive signals from the timer 72 and, optionally, the vacuum sensor 74. When using a visual display 52 as the output unit, the measured duration will be displayed. Additionally, the measured level of the applied vacuum may be displayed through the display 52 as depicted in FIG. 3. Both duration of vacuum application and vacuum magnitude may be displayed simultaneously, or alternatively. When utilizing an output port 54, the signal may be transmitted to a separate display, recording device, both, or a combination thereof.

Monitoring device 50 as described herein may be configured to operate in various ways and provide multiple functions. For example, in one embodiment, upon closing of a switch responsive to application of at least a specified magnitude of vacuum, the timer 72 of monitoring device 50 clocks the duration of a vacuum as applied at a specified level and exhibits that duration through the visual display 52 for observation by the clinician. Upon release of the vacuum completely or below a certain magnitude, the switch opens, the display may zero or darkens and the timer 72 resets to zero to measure the duration of a subsequent, newly applied vacuum. Thus, in one configuration, the monitoring device 50 is configured to monitor and output the duration of individual, discrete and specific applications of an applied vacuum above a certain selected magnitude by vacuum assisted fetal extraction apparatus 10. The timer 72 may be structured so as to trigger an alarm or other indicator (e.g., a flashing light) upon reaching a specified elapsed time or duration of vacuum application above a certain threshold magnitude. For example, the display 52 might include a beeping or chirping audio alarm or an LED or similar bright, visual indicator to alert the clinician.

In another aspect of the invention, a pressure or vacuum sensor 74 might be utilized to measure the level of applied vacuum in substantially real time and generate an output signal to be exhibited on the visual display 52. Likewise, as with timer 72, an alarm might be incorporated into pressure or vacuum sensor 74 or otherwise placed in circuit 70 and set to respond to a certain magnitude of output signal from pressure or vacuum sensor 74 to alert the operator that the magnitude of vacuum applied through vacuum cup 12 to the fetus' head has exceeded or is approaching a specified threshold limit. Such a device configuration allows the clinician to be informed as to not only the duration but also the magnitude of stress in the form of vacuum being applied to a fetus' head during delivery.

A similar but slightly more complex configuration of the monitoring device 50 allows measurement of the cumulative duration of a series of applications of vacuum through vacuum cup 12 of a vacuum assisted fetal extraction apparatus of the invention to the fetus' head. For example, upon initiation of a vacuum in a first application thereof to the fetus, a switch is closed and the timer 72 will clock the duration thereof and, upon release or relaxation of the vacuum to at least a certain selected lower threshold, the switch is opened and the timer 72 will stop or pause. The timer 72, instead of zeroing will, however, retain the clocked duration of vacuum application and add to it each time the switch is closed. Alternatively, the circuit 70 may include nonvolatile memory enabling retention of each duration of applied vacuum as clocked by timer 72 and a logic circuit to direct accumulation of multiple such durations output by timer 72 into the memory. In either case, upon each initiation of a new application of a vacuum above a selected threshold, the timer 72 will begin clocking the duration of such new application so that the durations are additive or cumulative. Thus, for example, if the first application has a duration of six minutes, the second application will initiate clocking starting at a value of six minutes. If the second application has a duration of five minutes, a third application would then start measuring the duration at a value of eleven minutes, and so on, thus measuring a cumulative duration of applied vacuum. Such a configuration would allow for total duration of vacuum force A applied during the delivery of the fetus to be monitored and recorded. The monitoring device 50 may be configured to operate in either mode as described above and a mode reset button optionally employed such that the monitoring device 50 might be utilized according to either of the disclosed timing configurations.

As noted above, the number of times traction is applied to an infant's skull is also of significant interest. As described previously, the number of tractions may be monitored by the number of times the timer 72 is activated and then deactivated, which corresponds to the number of times a vacuum (of any sort or above a certain selected magnitude to be sensed) is generated in the system so that traction may be applied and then released. Alternatively and perhaps more directly indicative of the application of traction to the infant, fluctuation of vacuum level in the closed system of an extraction apparatus responsive to the application of traction may be sensed. Alternatively, a force sensor, such as, for example a strain gage 80 indicated schematically in broken lines in FIG. 1, may be employed to provide a traction signal to the microprocessor associated with timer 72 when traction force is applied through tubing 16 when hand pump 14 is pulled after a sufficient vacuum exists in vacuum cup 12.

Another, further configuration for monitoring device 50 is to configure the timer 72 to measure a cumulative duration of applied vacuum over a rolling time period. In such a configuration, a specified or defined period of time would be selected. As an example, one hour may be specified as the rolling time period. Once initiated, the timer would then measure a cumulative duration of a series of applications of vacuum by the vacuum assisted fetal delivery device within the most recent one hour period. For example, if a vacuum duration of ten minutes is measured upon initial activation of the monitoring device 50 during a delivery and one hour has been specified as the rolling time period, the initial ten minute duration of vacuum application will be included in the cumulative duration one hour after activation, but it will not be included in a cumulative duration displayed or communicated to the operator one hour and ten minutes after initial activation of the apparatus to apply a vacuum. Thus, the monitoring device displays or communicates the amount of time the apparatus has been applying a vacuum above a threshold level only with respect to a preceding, specified time period. It is generally recognized that any cumulative application of vacuum sufficient to employ in extracting the infant exceeding twenty to, at most, thirty minutes is considered excessive and possibly abusive of vacuum extraction.

Figure 7:
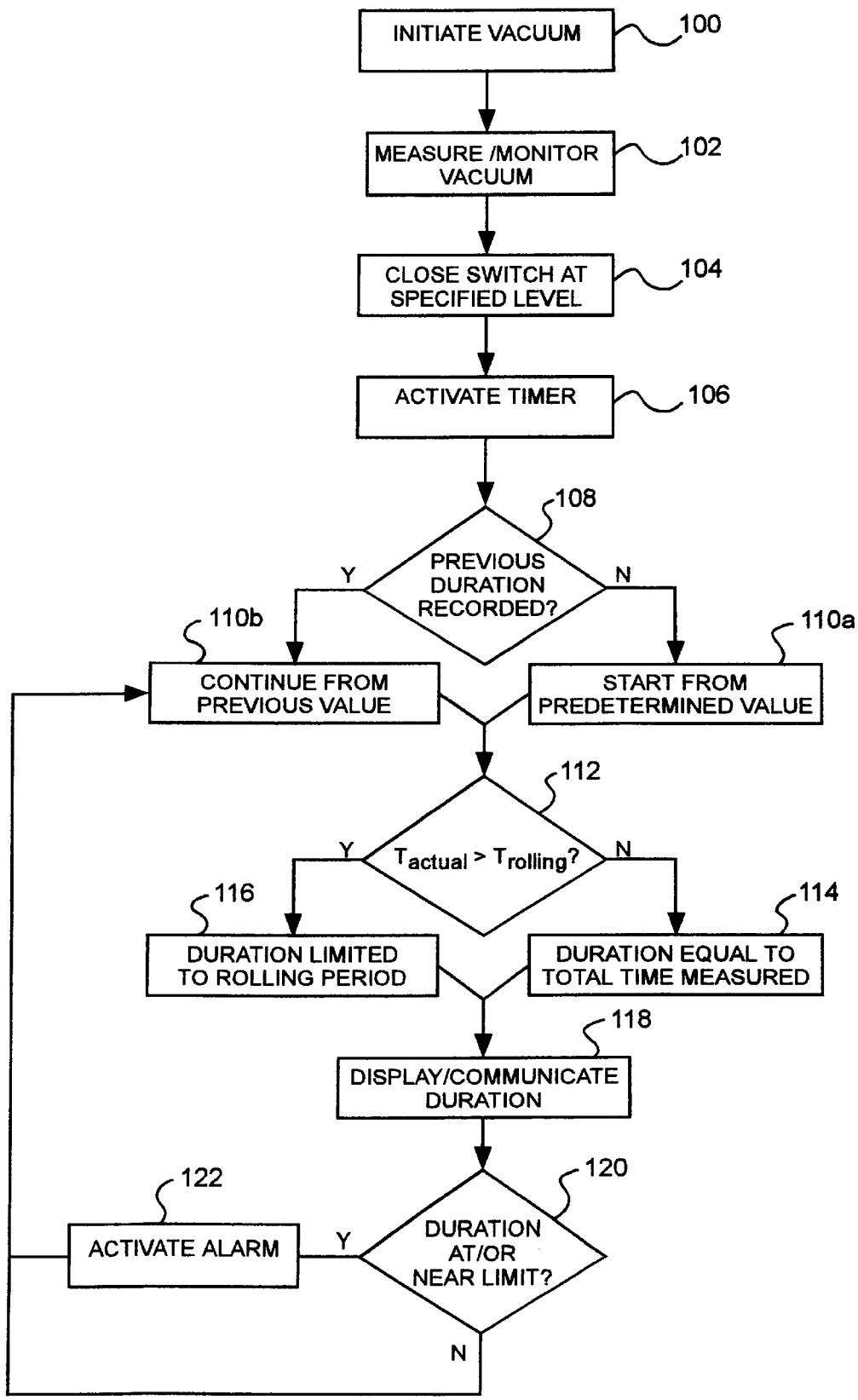
FIG. 7 is flow chart depicting the logic utilized according to one embodiment of the present invention.

The foregoing, more sophisticated configuration may be more fully understood and appreciated with reference to the logic diagram shown in FIG. 7. Upon employment of a vacuum assisted fetal extraction apparatus 10, 30 or 40, a vacuum is initiated as indicated at 100, the magnitude of which may be optionally monitored at 102 either absolutely or above a threshold level, as desired, using a sensor. As described above with respect to one embodiment, initiation of a vacuum may be employed to cause a switch to close at a certain magnitude of applied vacuum as shown at 104 which activates the timer at 106 to run until vacuum is released below the certain magnitude, causing the switch to open. In a monitoring device 50 employing a vacuum sensor used to monitor magnitude of the vacuum, an output signal thereof indicative of a vacuum above a certain magnitude may be used to activate the timer in lieu of a switch, the timer running until the vacuum is released below the certain magnitude or another selected magnitude. Thus, the timing function of monitoring device 50, whether switch or sensor initiated, is similar to a start/stop function of a lap timer. Once activated, the timer will then begin to clock the duration according to whether a previous duration has been recorded or not as indicated at 108. If a previous duration has not been recorded, for example, if either the monitoring device 50 has been reset or the vacuum assisted fetal extraction apparatus associated with the monitoring device 50 is being employed for the first time, then the timer will begin at a specified initial value as shown at 110a. The monitoring device 50 will preferably start at an initial value of zero and measure the duration as a positive value. However, it is also contemplated that an initial value may be set as an upper limit from which the duration of vacuum application will be subtracted, allowing the operator to see how much time is remaining during which the vacuum may remain, or be, applied to the fetus' head. If a previous duration has been recorded, then the monitor will continue from the previously measured value and a cumulative duration will result as indicated by 110b.

At this point in the logic, the monitoring device 50 determines whether the actual time elapsed since the first initiated vacuum, including durations when the vacuum is not applied, is greater than a specified rolling time period as shown at 112. If the actual time elapsed since the initial application of vacuum is less than the specified rolling time period, then the measured cumulative duration of vacuum application will simply be equal to the total time measured as indicated at 114. If, however, the actual time elapsed since application of the first vacuum is greater than the specified rolling time period, then the measured duration of vacuum application will be equal to the cumulative duration of vacuum applications measured during the most recent time period, for example, the most recent one hour, as shown at 116. Once the measured duration is determined, the duration will be displayed or otherwise communicated through an output device as indicated at 118. Although indicated at 120, at any time a determination may be made by monitoring device 50 as to whether the measured cumulative duration of vacuum application is at or near a specified limit which, most commonly, will be around twenty minutes. If the answer is in the affirmative, an alarm may optionally be activated as shown at 122. Each time the applied vacuum is released, the timer will be deactivated, stopping the clocking of applied vacuum duration. As used herein and as previously suggested, "release" of vacuum encompasses not only fully releasing the vacuum applied by vacuum cup 12 to the fetus' head but also diminishment or relaxation of vacuum to a preselected level lower than that employed when manipulating the fetus. For example, by using a vacuum sensor to activate and deactivate the timer, a microprocessor may be programmed to activate the timer at, for example, a vacuum of 450 mm Hg and to deactivate the timer when the vacuum is relaxed to, for example, the 100 to 150 mm Hg range. Thus, the vacuum cup 12 may remain secured to a fetus' head using a low, substantially benign vacuum level which may be readily increased to a level sufficient for manipulation of the fetus.

The logic as described above allows the operator of a vacuum assisted fetal extraction apparatus to be continually apprized of the cumulative duration of an applied vacuum within a specified time period. Such logic is helpful in implementing procedures or governmental regulations which require that a vacuum be applied for a specified cumulative duration within a specified time period, such as, for example specifying an allowable number of minutes within an hour period. While the precise permissible time period has not been uniformly established, presently about twenty minutes is believed by the inventor herein to comprise a preferable maximum.

In addition to the above-described embodiments and variations, it is also contemplated that the monitoring device 50 may include in memory variations in duration of applied vacuum in relation to variations in the level or magnitude of applied vacuum in the form of a composite index or scale for indicating whether the use of an applied vacuum is within a safe range. For example, it may be determined that an applied vacuum at a reduced level is sustainable for an extended period of time and the effect of such is similar to an applied vacuum at an increased level for a briefer period of time. With such a relationship, the measured magnitude value of the applied vacuum may be combined with the duration of the applied vacuum using closely intermittent real-time sampling intervals of, for example, one second, such as through a defined mathematical transfer function performed by the microprocessor of the timer or otherwise in the circuit by a separate component having such capability, to yield a single composite value representative of the effects of the applied vacuum to the fetus. Thus, a representative scale, or index of a range of such values, may be used to reveal to the clinician the combined effects of duration and magnitude of an applied vacuum to simplify the task of monitoring the effects of such. In addition, a warning signal or sequence of audible or visible signals may be triggered as the magnitude of the composite value increases during a procedure.

It is also contemplated that the total elapsed time of applied vacuum may be visually indicated to the practitioner using an extraction apparatus according to the present invention using graphic or color indicia, or a combination thereof. For example, a visual display 52 may be provided with an indicia-type elapsed time indicator in addition to or in lieu of a numerical display, as shown in FIG. 3 in broken lines 82. Such indicator 82 may comprise an LED bar graph divided into three or more zones to indicate (by way of example only) safe, cautionary or unacceptable total duration of applied vacuum. Alternately, an LED which changes color from green to yellow to red at different voltage input levels may be employed as an indicator 82, such devices being commercially available. Of course, an LED bar graph that not only illuminates progressively as total vacuum duration increases but also changes color to emphasize elapsed time may also be employed as an indicator 82. With either color change and/or light segment illumination employed for indicator 82, a green light or single illuminated LED segment may be employed to indicate 0 to 15 minutes total elapsed vacuum time, while more than 15 but less than 20 minutes total elapsed time may be indicated with a yellow light or two lighted LED segments, and greater than 20 minutes total elapsed time indicated with a red light of three lighted LED segments. As noted, both the number of segments and color change approach may be combined for further emphasis.

Thus, the present invention provides a miniaturized, disposable, low power requirement capability for monitoring duration and, optionally, magnitude of a vacuum applied to a fetus using a vacuum assisted fetal extraction apparatus. In one exemplary embodiment, the monitoring device may be sized as approximately 0.30 in.×0.15 in.×1.00 in., including display. An auto shut-off feature may cause the display to inactivate after a selected period of time after the timer is inactivated, for example, 60.0 minutes. A reset function, triggered, for example, by depression of a recessed button at the bottom of a small diameter hole by a needle or paper clip wire may be included in circuit 70 so that the timer and display may be re-zeroed as desired.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A monitoring device for a vacuum assisted fetal extraction apparatus, comprising:
   a circuit at least partially configured as a timer;
   an output unit operably coupled to the circuit for receiving a signal indicative of at least one duration as measured by the timer; and
   a switch operably coupled to the circuit and configured to be responsive to generation of a differential pressure during use of the vacuum assisted fetal extraction apparatus to activate the timer.

2. The monitoring device of claim 1, wherein the monitoring device is configured to sealingly communicate the switch with a vacuum reservoir of a vacuum assisted fetal extraction apparatus wherein a vacuum is generated during use thereof.

3. The monitoring device of claim 2, wherein the switch is configured to actuate at a specified magnitude of differential pressure between ambient atmospheric and the internal portion of the vacuum assisted fetal extraction apparatus.

4. The monitoring device of claim 3, wherein the switch is configured to actuate at a differential pressure of approximately 450 mm Hg.

5. The monitoring device of claim 2, wherein the switch is a vacuum-actuated switch.

6. The monitoring device of claim 1, wherein the switch is activated responsive to movement of an element of a mechanical vacuum indicator in communication with a vacuum reservoir of a vacuum assisted fetal extraction apparatus wherein a vacuum is resident during use thereof.

7. The monitoring device of claim 1, wherein the timer is configured to measure the at least one duration in increasing increments.

8. The monitoring device of claim 7, wherein the timer is configured to measure the at least one duration in units of either minutes and seconds or minutes and tenths of seconds.

9. The monitoring device of claim 1, wherein the timer is configured to measure the at least one duration in decreasing increments from a predetermined initial value.

10. The monitoring device of claim 9, wherein the timer is configured to measure the at least one duration in units of either minutes and seconds or minutes and tenths of minutes.

11. The monitoring device of claim 1, wherein the output unit includes at least one display element selected from the group comprising a liquid crystal display (LCD), at least one light emitting diode and an analog display.

12. The monitoring device of claim 11, wherein the output unit includes at least one of a numerical display, a graphic indicia display and a changing color display.

13. The monitoring device of claim 1, wherein the output unit includes at least one of a numerical display, a graphic indicia display and a changing color display.

14. The monitoring device of claim 1, further including a port for operably coupling the monitoring device to an external circuit.

15. The monitoring device of claim 14, wherein the external circuit includes at least one of a display unit, a recording unit and a power supply.

16. The monitoring device of claim 1, wherein the switch is further configured to deactivate the timer upon relaxation of the differential pressure.

17. The monitoring device of claim 16, wherein the circuit is configured to cause the timer to activate at a first differential pressure and to deactivate at a second differential pressure.

18. The monitoring device of claim 17, wherein the first differential pressure is different than the second differential pressure.

19. The monitoring device of claim 16, wherein the switch comprises a differential pressure transducer configured to generate an output signal proportional to a magnitude of a sensed pressure differential.

20. The monitoring device of claim 1, wherein the timer is configured to clock the cumulative duration of multiple activations.

21. The monitoring device of claim 20, wherein the timer is configured to measure the cumulative duration of multiple activations during a predetermined time period.

22. The monitoring device of claim 20, wherein the timer is configured to measure the cumulative duration of multiple activations during a predetermined rolling time period.

23. The monitoring device of claim 20, wherein the timer is configured to monitor a total number of the multiple activations.

24. The monitoring device of claim 1, wherein the timer is configured to monitor a total number of activations thereof.

25. The monitoring device of claim 1, farther comprising an alarm operably coupled to the circuit and wherein the circuit is configured to trigger the alarm responsive to measurement by the timer of a predetermined time period.

26. The monitoring device of claim 25, wherein the predetermined time period comprises a cumulation of multiple, smaller time periods.

27. The monitoring device of claim 25, wherein the alarm includes at least one of a visible indicator and an audible indicator.

28. The monitoring device of claim 1, further comprising a pressure sensor operably coupled to the circuit and configured to generate a signal, responsive to which the output unit receives a signal representative of a measured differential pressure.

29. The monitoring device of claim 28, further comprising an alarm operably coupled to the circuit and wherein the circuit is configured to activate the alarm upon the generation of a signal by the pressure sensor indicative of a differential pressure greater than a selected magnitude.

30. The monitoring device of claim 28, wherein the circuit is configured to provide a signal indicative of a maximum differential pressure measured during a predetermined time period.

31. The monitoring device of claim 1, further including a power supply operably coupled to the circuit and selected from the group consisting of a battery and an external source of line voltage.

32. The monitoring device of claim 1, wherein the output unit is configured to indicate at least one of time duration and magnitude of differential pressure.

33. The monitoring device of claim 32, wherein the output unit is configured for a manner of indication including at least one of numeric indication, graphic indication and change of color indication.

34. A monitoring device comprising:
a circuit at least partially configured as a timer;
a pressure sensor configured to generate a signal substantially indicative of a magnitude of sensed differential pressure, operably coupled to the circuit and configured to be operably coupled to a vacuum reservoir of a vacuum assisted fetal extraction apparatus wherein a vacuum exists during use thereof, the circuit being configured to activate the timer responsive to a signal generated by the pressure sensor indicative of a first selected magnitude of differential pressure and deactivate the timer responsive to a signal generated by the vacuum sensor indicative of a second selected magnitude of differential pressure;
wherein the circuit is configured to generate an output signal which employs as inputs at least one duration of timer activation in combination with at least one sensed magnitude of differential pressure; and
an output unit operably coupled to the circuit to at least output an indicia of the output signal.

35. The monitoring device of claim 34, wherein the output signal is generated responsive to the use of at least one transfer function.

36. A vacuum assisted fetal extraction apparatus comprising:
a vacuum cup configured for application to a portion of a fetus;
a selectively actuable vacuum source operably coupled to the vacuum cup for generating a vacuum therein;
a monitoring device comprising a circuit configured at least partially as a timer, a switch operably coupled with the circuit and responsive to generation of a vacuum to be applied by the cup to activate the timer and to deactivate the timer responsive to at least a partial release of vacuum after activation; and
an output unit for communicating at least a duration of timer activation.

37. The apparatus of claim 36, wherein the vacuum source is either manually or electrically operated.

38. The apparatus of claim 36, wherein the switch is configured to close at a specified magnitude of sensed differential pressure.

39. The apparatus of claim 36, wherein the switch is configured to close at a sensed differential pressure of about 450 mm Hg.

40. The apparatus of claim 36, wherein the switch is a differential pressure responsive switch.

41. The apparatus of claim 36, further comprising a mechanically actuated vacuum indicator and wherein the switch is actuable responsive to movement of an element of the vacuum indicator.

42. The apparatus of claim 36, wherein the timer is configured to measure the duration in increasing increments.

43. The apparatus of claim 42, wherein the timer is configured to measure the duration in units of either minutes and seconds or minutes and tenths of minutes.

44. The apparatus of claim 36, wherein the timer is configured to measure the duration in decreasing increments from a preselected initial value.

45. The apparatus of claim 44, wherein the timer is configured to measure the duration in units of either minutes and seconds or minutes and tenths of minutes.

46. The apparatus of claim 36, wherein the output unit includes at least one of a liquid crystal display (LCD), at least one light emitting diode (LED), and an analog display.

47. The apparatus of claim 46, wherein the output unit includes at least one of a numerical display, a graphic indicia display and a changing color display.

48. The apparatus of claim 36, wherein the output unit includes at least one of a numerical display, a graphic indicia display and a changing color display.

49. The apparatus of claim 36, further including a port for operably coupling the output unit to an external circuit.

50. The apparatus of claim 49, wherein the external circuit includes at least one of a display unit, a recording unit and power supply.

51. The apparatus of claim 36, wherein the circuit is configured to cause the timer to activate at a first differential pressure and to deactivate at a second differential pressure.

52. The apparatus of claim 51, wherein the first differential pressure is different than the second differential pressure.

53. The apparatus of claim 52, wherein the switch comprises a differential pressure transducer configured to generate an output signal proportional to a magnitude of a sensed pressure differential.

54. The apparatus of claim 36, wherein the timer is configured to clock a cumulative duration of multiple activations.

55. The apparatus of claim 54, wherein the timer is configured to measure the cumulative duration of multiple activations during a predetermined time period.

56. The apparatus of claim 54, wherein the timer is configured to measure the cumulative duration of multiple activations during a predetermined rolling time period.

57. The apparatus of claim 54, wherein the timer is configured to monitor a total number of the multiple activations.

58. The apparatus of claim 36, wherein the timer is configured to monitor a total number of activations thereof.

59. The apparatus of claim 36, further comprising an alarm operably coupled to the circuit and wherein the circuit is configured to trigger the alarm responsive to measurement by the timer of a predetermined time period.

60. The apparatus of claim 59, wherein the predetermined time period comprises acumulation of multiple, smaller time periods.

61. The apparatus of claim 59, wherein the alarm includes at least one of a visible indicator and an audible indicator.

62. The apparatus of claim 36, further comprising a pressure sensor operably coupled to the circuit and configured to generate a signal, responsive to which the output unit receives a signal representative of a measured differential pressure.

63. The apparatus of claim 62, further comprising an alarm operably coupled to the circuit and wherein the circuit is configured to activate the alarm upon the generation of a signal by the pressure sensor indicative of a differential pressure greater than a selected magnitude.

64. The apparatus of claim 62, wherein the circuit is configured to provide a signal indicative of a maximum differential pressure measured during a predetermined time period.

65. The apparatus of claim 36, further including a power supply operably coupled to the circuit and selected from the group consisting of a battery and an external source of line voltage.

66. The apparatus of claim 36, wherein the output unit is configured to indicate at least one of time duration and magnitude of differential pressure.

67. The apparatus of claim 66, wherein the output unit is configured for a manner of indication including at least one of numeric indication, graphic indication and change of color indication.

68. A method of monitoring the use of a vacuum assisted fetal extraction apparatus, comprising:

applying a vacuum to a portion of a fetus at least one time;

detecting the at least one application of the vacuum;

measuring a duration of the at least one application of the vacuum; and communicating the measured duration of the at least one application of the vacuum.

69. The method of claim 68, wherein measuring the duration of the at least one application of the vacuum includes selecting a time period and measuring the cumulative duration of the at least one application of the vacuum during the selected time period.

70. The method of claim 68, wherein measuring the duration of the at least one application of the vacuum includes selecting a rolling time period and measuring the cumulative duration of the at least one application of the vacuum during the rolling time period.

71. The method of claim 70, wherein communicating the measured duration of the at least one application of the vacuum includes communicating the cumulative duration of the at least one application of the vacuum during the rolling time period.

72. The method of claim 68, wherein communicating the measured duration of the at least one application of the vacuum includes outputting an indicia of the measured duration on a visual display.

73. The method of claim 72, wherein outputting the indicia of the measured duration on the visual display comprises at least one of outputting numerically, graphically, and by color change.

74. The method of claim 68, further comprising detecting a magnitude of the at least one application of the vacuum and communicating the detected magnitude to an operator.

75. The method of claim 74, wherein communicating the detected magnitude of the at least one application of the vacuum includes outputting an indicia of the detected magnitude on a visual display.

76. The method of claim 75, wherein outputting the indicia of the detected magnitude on the visual display comprises at least one of outputting numerically, graphically, and by color change.

77. The method of claim 68, further comprising triggering an alarm to alert an operator upon exceeding at least one of a predetermined magnitude or duration of applied vacuum.

78. The method of claim 68, further including employing a detected magnitude of the at least one application of the vacuum in combination with the measured duration of the at least one application of the vacuum to generate a composite index or scale representative of allowable vacuum assistance.

79. The method of claim 78, further comprising triggering an alarm to alert an operator upon exceeding a predetermined value of the composite index or scale.

80. The method of claim 68, wherein the at least one application comprises a plurality of applications.

* * * * *

UNITED STATES PATENT AND TRADEMARK OFFICE
CERTIFICATE OF CORRECTION

PATENT NO. : 6,468,284 B1
DATED : October 22, 2002
INVENTOR(S) : William Dean Wallace It is certified that error appears in the above-identified patent and that said Letters Patent is hereby corrected as shown below:

<u>Title page, Item [54] and Column 1, line 1,</u>
Title, change "VACCUM" to -- VACUUM --

<u>Column 3,</u>
Line 38, after "of" delete "A"

<u>Column 6,</u>
Line 45, after "according" and before "the" insert -- to --

<u>Column 7,</u>
Line 17, change "alternatively" to -- alternately --

<u>Column 8,</u>
Line 17, after "force" delete "A"

<u>Column 12,</u>
Line 46, change "farther" to -- further --

Signed and Sealed this

Twelfth Day of August, 2003

JAMES E. ROGAN
*Director of the United States Patent and Trademark Office*